United States Patent [19]
Koziol

[11] Patent Number: 5,425,727
[45] Date of Patent: * Jun. 20, 1995

[54] BEAM DELIVERY SYSTEM AND METHOD FOR CORNEAL SURGERY

[76] Inventor: Jeffrey E. Koziol, 1211 S. Arlington Heights Rd., Arlington Heights, Ill. 60005

[*] Notice: The portion of the term of this patent subsequent to Dec. 24, 2008 has been disclaimed.

[21] Appl. No.: 132,836

[22] Filed: Oct. 7, 1993

Related U.S. Application Data

[63] Continuation-in-part of Ser. No. 944,431, Sep. 14, 1992, abandoned, which is a continuation-in-part of Ser. No. 812,163, Dec. 23, 1991, abandoned, which is a continuation of Ser. No. 598,793, Oct. 17, 1990, Pat. No. 5,074,859, which is a continuation of Ser. No. 464,637, Jan. 5, 1990, abandoned, which is a continuation of Ser. No. 176,765, Apr. 1, 1988, abandoned.

[51] Int. Cl.$^6$ .............................................. A61N 5/06
[52] U.S. Cl. ........................................ 606/5; 606/10; 606/13; 606/17; 606/18
[58] Field of Search ............................... 606/2–6, 606/10–19

[56] References Cited

U.S. PATENT DOCUMENTS

| | | | |
|---|---|---|---|
| 3,821,510 | 6/1974 | Muncheryan | 219/121.79 |
| 3,931,491 | 1/1976 | Stampf | 219/121.67 |
| 4,002,877 | 1/1977 | Banas | 219/121.72 |
| 4,028,525 | 6/1977 | Mominee et al. | 219/121.78 |
| 4,315,130 | 2/1982 | Inagaki et al. | 219/121.73 |
| 4,356,375 | 10/1982 | Josephy et al. | 219/121.73 |
| 4,370,540 | 1/1983 | Davis et al. | 219/121.85 |
| 4,409,979 | 10/1983 | Roussel et al. | 128/303.1 |
| 4,461,294 | 7/1984 | Baron | 128/303.1 |
| 4,518,232 | 5/1985 | Dagenais | 219/121.74 |
| 4,648,400 | 3/1987 | Schneider et al. | 128/303.1 |
| 4,658,109 | 4/1987 | Honeycutt et al. | 219/121.73 |
| 4,665,913 | 5/1987 | L'Esperance, Jr. | 128/303.1 |
| 4,669,466 | 6/1987 | L'Esperance | 128/303.1 |
| 4,712,543 | 12/1987 | Baron | 128/303.1 |
| 4,720,619 | 1/1988 | Mattei et al. | 219/121.77 |
| 4,724,522 | 2/1988 | Belgorod | 364/415 |
| 4,729,372 | 3/1988 | L'Esperance, Jr. | 128/303.1 |
| 4,732,148 | 3/1988 | L'Esperance, Jr. | 128/303.1 |
| 4,887,592 | 12/1989 | Loerlecher | 606/18 |
| 4,941,093 | 7/1990 | Marshall et al. | 606/5 |
| 5,074,859 | 12/1991 | Koziol | 606/5 |

FOREIGN PATENT DOCUMENTS

| | | |
|---|---|---|
| 2594686 | 8/1987 | France . |
| 8707165 | 12/1987 | WIPO ............................... 128/303.1 |

OTHER PUBLICATIONS

"Response of the Corneal Epithelium to KrF Excimer Laser Pulses", by J. Taboda et al; Health Physics, vol. 40, May 1981, pp. 677–683.

Primary Examiner—David M. Shay
Attorney, Agent, or Firm—Roylance, Abrams, Berdo & Goodman

[57] ABSTRACT

An apparatus and method for delivering radiant energy beams onto an area of a cornea in a line focus to create a linear incisions. The radiant energy beams may be focused in a linear configuration onto the external surface of the cornea or onto intrastromal areas of the cornea of an eye to ablate the cornea in a radial slot, circumferential curved slot, or lenticular pattern, and thereby modify its curvature and refractive power. The apparatus includes an array of central reflectors and an assembly of peripheral reflectors. Each central reflector is associated with a respective peripheral reflector so that a beam reflected by the central reflector is intercepted by its associated peripheral reflector and is again reflected to precisely incise either external or internal areas of the cornea. Each peripheral reflector has a curved reflective surface to provide a line focus on the cornea, including both rectilinear and curvilinear line focus to create radial and circumferential curved incisions. In a modified embodiment, the assembly of peripheral reflectors and the array of central reflectors rotate to permit lathing of the cornea.

34 Claims, 8 Drawing Sheets

BEAM DELIVERY SYSTEM AND METHOD FOR CORNEAL SURGERY

RELATED APPLICATIONS

This is a continuation-in-part application of Ser. No. 07/944,431 filed on Sep. 14, 1992, now abandoned, which is a continuation-in-part of Ser. No. 07/812,163 filed on Dec. 23, 1992, now abandoned, which is a continuation of Ser. No. 07/598,793 filed on Oct. 17, 1990, now U.S. Pat. No. 5,074,859, which is a continuation of Ser. No. 07/464,637 filed on Jan. 5, 1990, now abandoned, which is a continuation of Ser. No. 07/176,765 filed on Apr. 1, 1988, now abandoned.

FIELD OF THE INVENTION

The invention relates to an apparatus for delivering radiant energy beams onto the cornea of an eye. More specifically, the invention relates to an array of central reflectors for intercepting a radiant energy beam and reflecting and splitting the beam along several paths to an assembly of peripheral reflectors radially spaced therefrom, which in turn focus and reflect the beams onto the cornea in line configurations. The central reflector and the peripheral reflector assembly can be moved as a single unit relative to the eye for scanning operations. The invention when used in a stationary position can ablate the cornea via simultaneously applied radial or circumferential incisions, and when moved can re-profile the cornea via photolathing. A stationary line or circle can be scanned across the cornea either by moving the central and peripheral reflectors relative to the cornea, or by moving the lenses in front of the central reflector for reprofiling or shaping the cornea via photoablation.

BACKGROUND OF THE INVENTION

The use of high intensity light sources such as lasers for cutting and reshaping eyes has expanded in recent years in part due to the superior precision, controllability and safety which such cutting technology offers over other cutting technologies, such as mechanical cutting of the eye. One type of ophthalmic surgical procedure for which high-intensity light radiation is particularly well suited is the radial keratotomy procedure in which a number of radial incisions are made on the cornea of the eye to change the curvature of the cornea.

Several methods and apparatus for performing radial keratotomies with lasers have been proposed. See, for example, U.S. Pat. No. 4,648,400 to Schneider et al; and U.S. Pat. No. 4,665,913 to L'Esperance, Jr. Schneider et al describe the use of lasers to selectively ablate the cornea of the eye by directing the laser beam through a generally planar mask having radial slots. The radial slots of the mask permit portions of the laser beam to pass through the mask and incise the cornea in a pattern of circumferentially spaced radial incisions.

Lasers have also been used to ablate an annular portion of the cornea by scanning or variably attenuating the laser beam. Such scanning changes the front surface of the cornea to a different optical curvature, thereby changing the refraction of the eye. See, for example, U.S. Pat. No. 4,669,466 to L'Esperance.

In such an application, it is desirable to deliver uniform beam energy along the curved scanning path. However, since the cornea presents a convexly curved surface to the laser beam, the outer circumferential portions of the cornea lie at further distances from the beam source than those portions at or near the center of the cornea. Thus, the laser beam incidents the cornea with a different angle along the cornea's constantly changing surface which causes variation of the energy density of the laser beam in a direction perpendicular to the corneal surface.

Using a mask to produce corneal incisions does not focus the beam on the corneal surface but merely projects the beam toward the surface.

Additionally, the energy of the laser beam may not be distributed uniformly due to the position of the mask relative to the beam or due to inherent non-uniformity of the laser beam itself. A non-uniform distribution of energy results in differing depths of the radial incisions, leading to an improper restructuring of the curvature of the cornea.

More recently, laser systems have been developed to ablate intrastromal areas of a cornea without ablating or piecing the external surface of the cornea. These laser systems focus the lower beams as a spot on the intrastromal areas of the cornea to be ablated. Thus, to create a linear incision, the laser must ablate a plurality of spots along the line of incisions. An example of a laser system employing spot focus ablation is disclosed in U.S. Pat. No. 4,907,586 to Bille et al, which is hereby incorporated herein by reference.

SUMMARY OF THE INVENTION

Accordingly, a primary object of the present invention is to provide an apparatus and method for delivering radiant energy from a radiant energy source in a line focus onto an area of the cornea to create circular incisions.

An additional object of the invention is to create a line focus on the cornea which can be straight, curved, circular, oval or irregular and scanned across the cornea to produce optical surface changes which are smooth, precise and easily controlled. This can result in aspheric and multi-focal slopes in the corneal surface.

An additional object of the invention is to provide an apparatus and method for delivering radiant energy onto an eye which minimizes the energy needed to incise the cornea to a desired depth via focusing of the radiant energy.

Another object of the invention is to provide an apparatus and method for controlling radiant energy to produce optical changes in an eye and maintain substantially constant incision depth across the incision.

Another object of the invention is to provide an apparatus and method of conducting corneal surgery via focusing laser light and thus concentrate the laser energy 100 to 10,000 times to permit use of low cost lasers such as a frequency modified 5th Harmonic YAG laser or very short duration nanosecond and picosecond lasers can be used.

The foregoing objects are basically attained by providing an apparatus for delivering radiant energy beams onto the cornea of an eye centered on a main optical axis, comprising a source of a radiant energy beam aimed along the main optical axis for emitting a radiant energy beam having a wavelength capable of ablating a predetermined area of the cornea of an eye; a support; central reflector arranged about the main optical axis for intercepting the radiant energy beam incident thereon, splitting the beam into a ring-shaped beam, and reflecting the ring-shaped beam outwardly of the main optical axis; a first member coupled to the support and the central reflector for coupling the central reflector to the support; peripheral reflector outwardly spaced from the central reflector for intercepting the ring-shaped beam reflected from said central reflector and for directing the ring-shaped beam generally along the main optical axis and incident onto the cornea; a second member coupled to the support; and the peripheral reflector for coupling the peripheral reflector to the support; and a mechanism for focusing the intercepted beam portion onto an area on the cornea in a ring-shaped configuration.

The foregoing objects are also attained by providing a method of ablating a cornea via a radiant energy beam comprising the steps of aligning a source of a radiant energy beam and the cornea along a main optical axis, emitting the radiant energy beam from the source, splitting the beam into a continuous ring-shaped beam and reflecting the ring-shaped beam outwardly of the main optical axis, and reflecting the outwardly directed ring-shaped beam to produce output beam portions incident on the cornea in a linear, ring-shaped configuration.

The foregoing objects are also attained by the method of reprofiling a cornea via a radiant energy beam by moving the position of the central and peripheral reflectors to cause the linear focused light to be scanned across the cornea. The angle of light intercepting the central mirror can also be changed by moving lenses in front of the central reflector to cause the linear focused light to be scanned across the cornea.

Other objects, advantages and salient features of the invention will become apparent from the following detailed description, which, taken in conjunction with the annexed drawings, discloses preferred embodiments of the invention.

BRIEF DESCRIPTION OF THE DRAWINGS

Referring now to the drawings which form a part of this original disclosure.

DETAILED DESCRIPTION OF PREFERRED EMBODIMENTS

Figure 1:
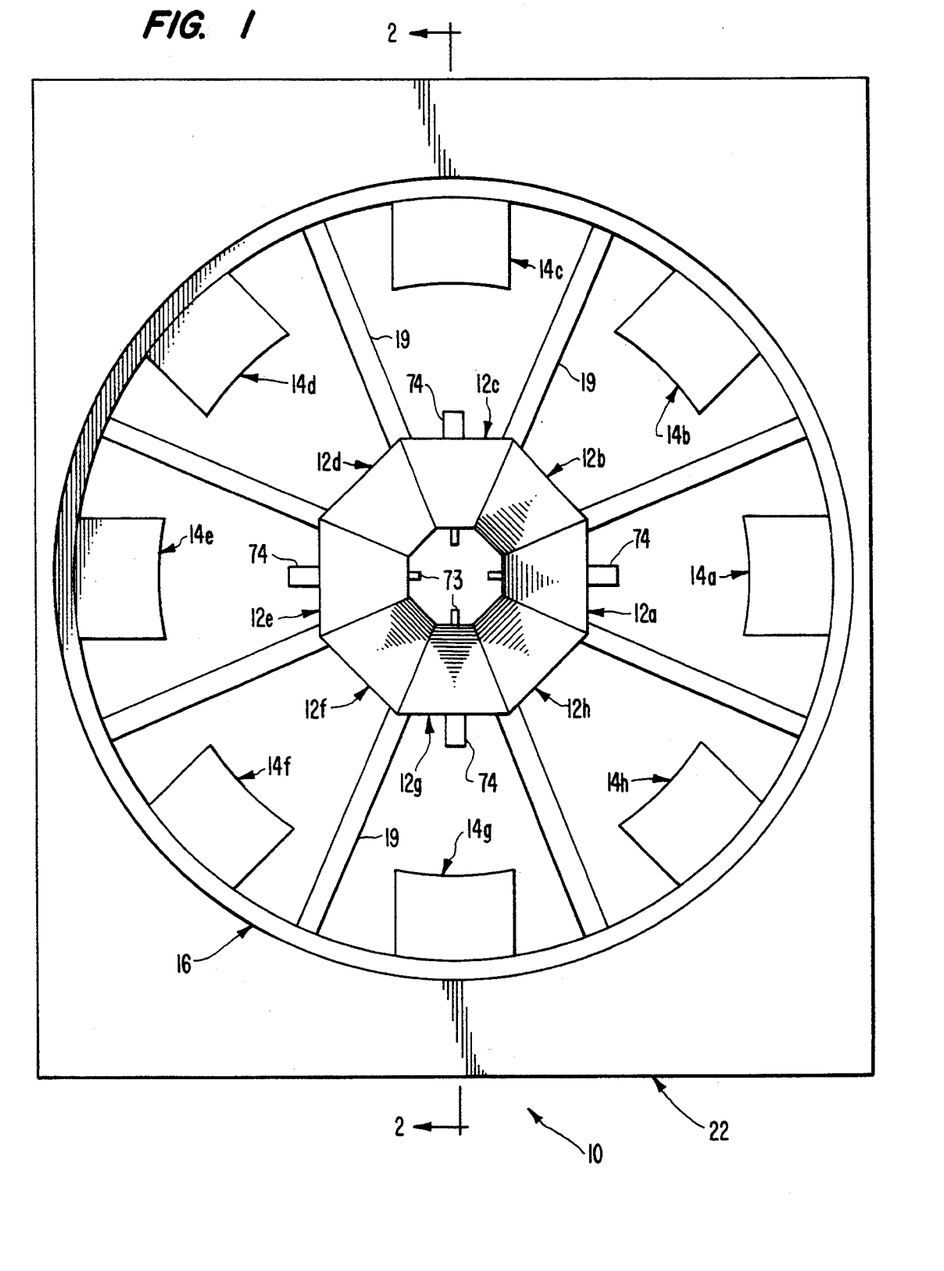
FIG. 1 is a front plan view of the beam delivering apparatus of the present invention, showing an array of central reflectors, each having an associated peripheral reflector radially and axially spaced from it.
Figure 2:
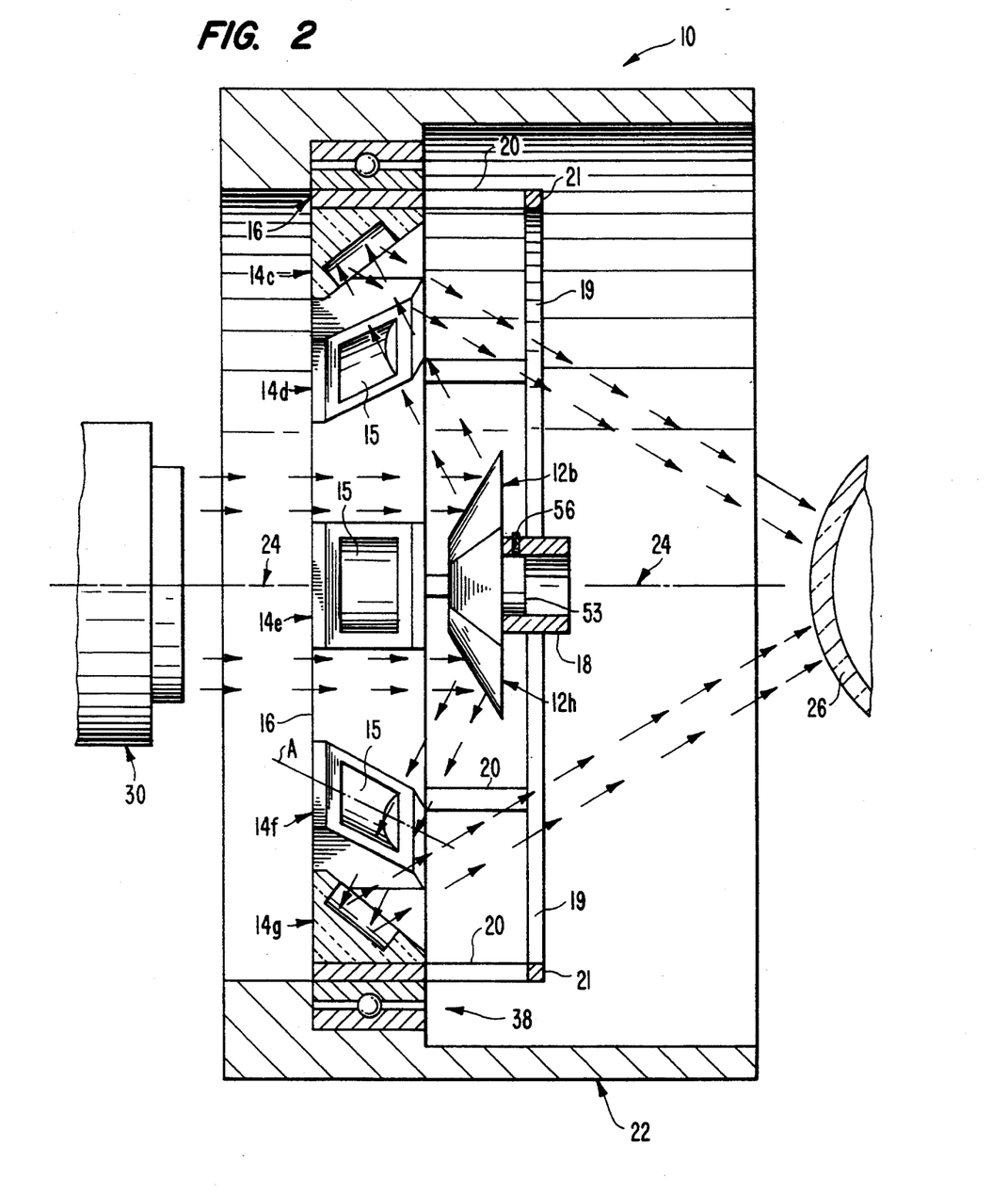
FIG. 2 is a cross-sectional side view of the beam directing apparatus of FIG. 1, taken along line 2—2 in FIG. 1 and showing the apparatus aligned between a laser beam source and the cornea of an eye.

As seen in FIG. 1, a beam delivering apparatus 10 for focusing beams of radiant energy in a linear configuration is illustrated in accordance with a first embodiment of the present invention, and basically includes an annular array of central reflectors 12a–h and an annular assembly of peripheral reflectors 14a–h. Peripheral reflectors 14a–h are rigidly coupled to a rim 16. As seen in FIG. 2, rim 16 is rigidly coupled to a hub 18 by radial spokes 19, axial rods 20 and a ring 21. Central reflectors 12a–h are coupled to hub 18.

Beam delivering apparatus 10 is rotatably supported within a support or frame 22 about a main optical axis 24 which passes through the center of a cornea 26 of an eye. A laser beam source 30, such as a frequency modified 5th Harmonic YAG laser for ablating external surface areas of the cornea or a frequency-doubled YAG laser for ablating intrastromal areas of the cornea, is positioned to emit a beam along axis 24 and against central reflectors 12a–h. These reflectors split and reflect the beam onto peripheral reflectors 14a–h which then focus and reflect the split beams onto cornea 26.

Beam delivering apparatus 10 can be modified in a number of ways to adapt it for use in particular types of ophthalmic surgery. For example, beam delivering apparatus 10 can be modified to perform radial keratotomy operations on the external surface of cornea 26 or on intrastromal areas of cornea 26.

Referring now more specifically to the construction and orientation of central reflectors 12a–h and peripheral reflectors 14a–h for the radial keratotomy operation, a number of equal sized central reflectors 12a–h are provided and, preferably, the number of central reflectors is an even number more than two and less than 16, such as eight. As shown in FIG. 1, eight equally sized central reflectors 12a–h are rigidly coupled to one another along their sides in a octagonal array. As seen in FIG. 2, each central reflector 12a–h is oriented to present a slanted, outwardly facing flat surface to the beam emanating from beam source 30. The angle of each surface is about 50°–60° to axis 24.

Each peripheral reflector 14a–h is associated with one of central reflectors 12a–h and is oriented so that its reflective surface 15, which is curved and preferably semi-cylindrical about central axis A as seen in FIG. 2 and angled at about 40°–50° to axis 24, intercepts the beam reflected radially, outwardly by its associated central reflector. Axis A intersects main optical axis 24 at an acute angle of about 40°–50°. Additionally, each peripheral reflector is oriented so as to reflect the intercept beam axially and radially inward and to focus the beam into line focus either onto the external surface of cornea 26 or onto an intrastromal area of the cornea. The reflective surfaces of the central and peripheral reflectors can be mirrors or other reflective material. For example, the peripheral reflectors can be replaced with holographic elements.

Figure 6:
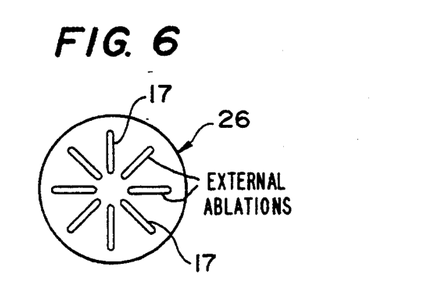
FIG. 6 is a schematic view of a cornea having radial incisions produced by a laser beam source in conjunction with the apparatus of FIGS. 1–3.
Figure 8:
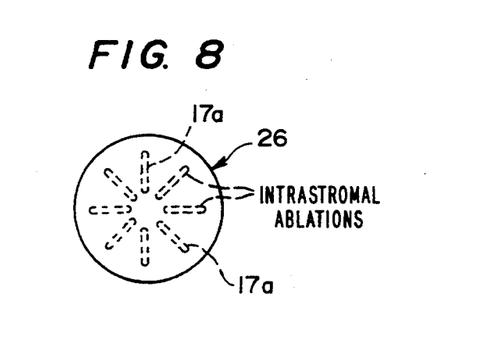
FIG. 8 is a schematic view of a cornea having intrastromal radial incisions produced by a laser beam source in conjunction with the apparatus of FIGS. 1–3.

As schematically shown in FIG. 6, a number of radial incisions 17 are cut via photoablation in the external surface of cornea 26 during the radial keratotomy operation. Alternatively, a number of radial, intrastromal incisions 17a can be cut via photoablation in intrastromal areas of cornea 26 during a radial keratotomy operation, as schematically illustrated in FIG. 8.

Beam delivering apparatus 10 can be used to produce the external or intrastromal incisions simultaneously. As seen in FIG. 1, each central reflector 12a–h intercepts the beam and reflects the beam towards its associated peripheral reflector. Central reflectors 12a–h are preferably rotatably coupled to hub 18 via an axle 53 fitting into the hub 18 and a screw adjustment assembly including three set screws 56 to lock the reflectors relative to hub 18. Central reflectors 12a–h can be moved as a single unit relative to hub 18 and the adjustment screws 56 can then be operated to adjust and fix the relative position of the central reflectors relative to the peripheral reflectors.

The combination of central and peripheral reflectors including the rim 16, hub 18, spokes 19, rods 20 and ring 21 are supported for rotation relative to frame 22 via ball bearing assembly 38, which is coupled to the frame and to rim 16. Thus, the angular position of the reflectors relative to the cornea and axis 24 can be varied. This allows angular placement as desired of either external incisions 17 on the cornea or intrastromal incisions 17a in the cornea.

The operation of beam delivering apparatus 10 during a simple radial keratotomy operation is as follows. Cornea 26 is immobilized by appropriate means and laser beam source 30 is positioned to emit a beam along main optical axis 24, which passes through the center of cornea 26. Beam directing apparatus 10 is positioned between beam source 30 and cornea 26 and is appropriately spaced from cornea 26 so that the beams reflected by the central and peripheral reflectors ablate cornea 26 in a pattern comprising separate and discrete areas of ablation shown in FIG. 6 or FIG. 8. Once beam directing apparatus 10 is positioned, a test beam can be emitted to test the alignment of the beams on cornea 26. Beam source 30 is then operated to emit a radiant energy beam, such as a laser beam, which travels along axis 24, encounters the central reflectors 12a–h, is split and radially reflected against peripheral reflectors 14a–h and is then again radially reflected and focused either onto the external surface of cornea 26 to simultaneously make external incisions 17 or onto intrastromal areas of cornea 26 to simultaneously make intrastromal incisions 17a.

Figure 3:
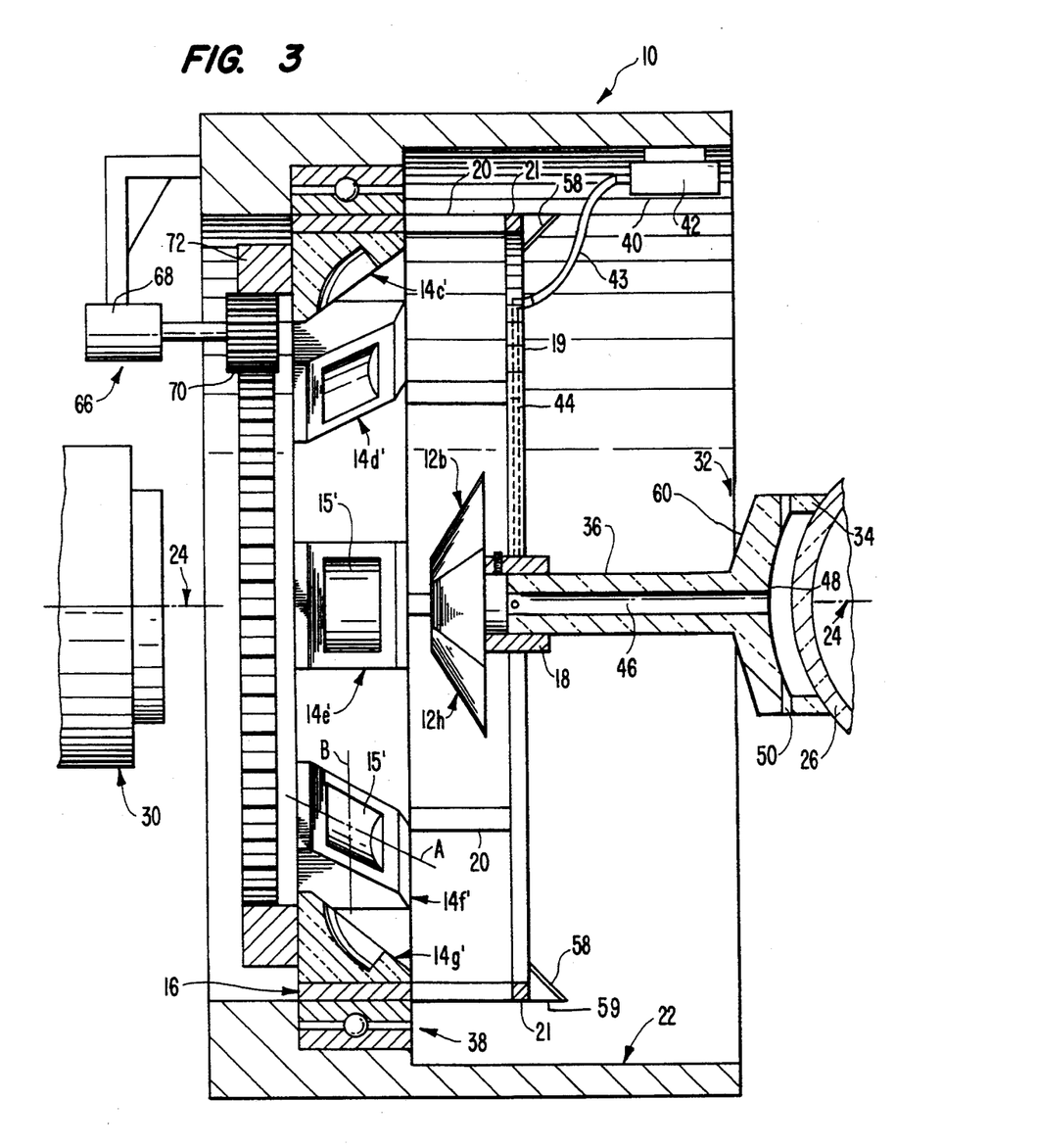
FIG. 3 is a cross-sectional side view of a modification of the apparatus of FIG. 1, having a gas conduit system for delivering gas to the ablated surface of the eye, a cornea alignment receptacle for positioning the cornea and a detection system for detecting the beam power density distribution as well as a motive assembly to rotate the reflectors.

Embodiment of FIG. 3

With reference especially to FIG. 3, beam delivering system 10 can have added to it an eye positioning device 32, coaxial with main optical axis 24 and coupled to hub 18. Eye positioning apparatus 32 has a concave surface 34, preferably having a radius of curvature the same as the average radius of curvature of a cornea, so that cornea 26 can be pressed against concave surface 34 and steadied in a fixed position during the eye operation. Eye positioning apparatus 32 is coupled via a connecting stem 36 to hub 18.

Eye positioning device 32 is preferably constructed of material which is transparent to the beam emitted by beam source 30 and permits complete through transmission of the beams reflected from the central and peripheral reflectors towards cornea 26.

Beam delivering apparatus 10 and eye positioning apparatus 32 can be provided with a gas or fluid conduit system 40 for delivering selected gases to the cornea 26 during ablation. Gas conduit system 40 includes a gas supply means 42 to supply gas along a tube 43 and a conduit 44 mounted within one of the spokes 19. Conduit 44 communicates with an axial conduit 46 within eye positioning apparatus 32 and axial conduit 46 communicates with a substantially semihemispheric recess 48 defined by concave surface 34. Recess 48 communicates with conduit 46 and cornea 26 and has outlets 50 for exhausting gases which have contacted cornea 26.

An inert gas such as argon can be supplied by gas conduit system 40 to contact cornea 26 and remove debris and other by-products of the surgical operation. Additionally, a gas or liquid having a cold temperature, such as, e.g., nitrous oxide, can be supplied by gas conduit system 40 to bathe cornea 26 in a cool environment and thereby lower the metabolic state of the cornea. Lowering the metabolic state of cornea 26 enhances the ability of the cornea to withstand traumatic insults from the beam.

To monitor the length and intensity of the beams directed onto the external surface of cornea 26 or onto the intrastromal areas of cornea 26 by apparatus 10, a plurality of linear detector arrays 58 can be installed. As seen in FIG. 3, apparatus 32 includes frustoconical surface 60 adapted to partially reflect a small portion (about 5%) of the beams directed towards cornea 26 by peripheral reflectors. Surface 60 further reflects these small portions of the beams against linear detectors 58 which are coupled to a detector means 59 for determining the beam intensity distribution and length. Preferably, three detectors 58 are used, which are rigidly coupled to ring 21.

As seen in FIG. 3, the peripheral reflectors 14a'–h' are modified from those shown in FIGS. 1 and 2 by having a curved reflective surface 15' curved about an axis B which is perpendicular to axis A. This curvature about axis B approximates the curvature of the external surface of the cornea being ablated and provides a more even ablation and beam intensity incident on the cornea. The radius of curvature of the reflective surface 15' about axis B reduces in the radially inward direction so the reflected line focus is substantially coincident or parallel to with the outer surface of the cornea. Reflective surface 15' is also curved and preferably semi-cylindrical about axis A.

Beam delivering apparatus 10 of FIG. 3 therefore permits more precision in the radial keratotomy procedure than existing systems which interpose a mask between the beam source and the cornea. Unlike the beams produced by the existing systems, each portion of the beam reaching cornea 26 is substantially uniformly focused on or in the cornea in a curved line focus. Thus, the distribution of energy along the incision is substantially uniform and can therefore be more precisely controlled.

Figure 4:
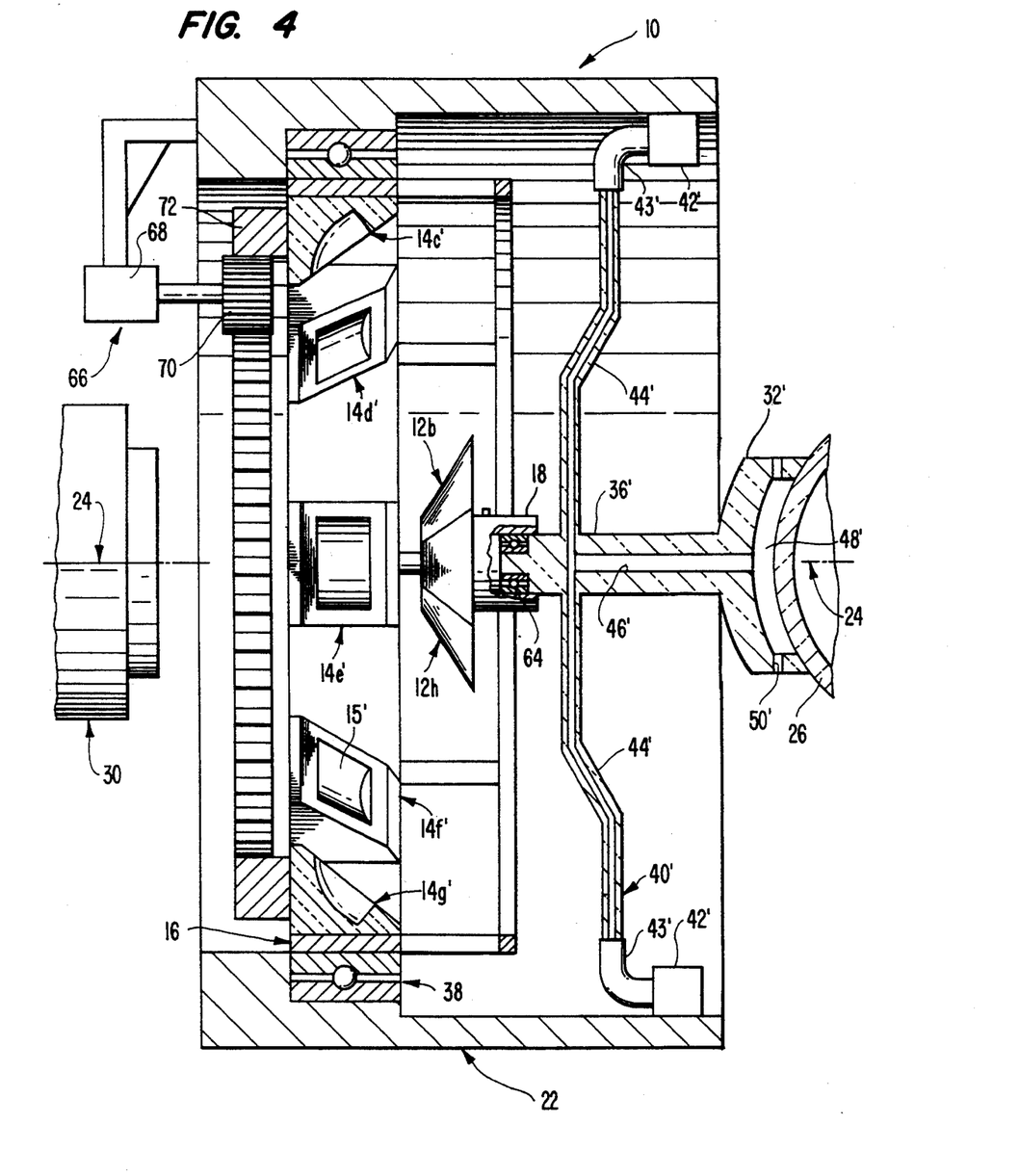
FIG. 4 is a cross-sectional side view of another modification of the apparatus of FIG. 1, showing a second gas conduit delivery system for delivering gas to the cornea of the eye during rotation of the reflectors.

Embodiment of FIG. 4

With reference now to the use of beam delivering apparatus 10 in an eye lathing, or scanning, operation as shown in FIG. 4, apparatus 10 can be especially adapted for scanning an eye. In the embodiment shown in FIG. 4, gas conduit system 40' is constructed with its conduits 44' remote from spokes 20, in contrast to the embodiment shown in FIG. 3 in which conduit 44 is formed within one of the spokes 19. Ball bearing assembly 64 is provided at the connection of connecting stem 36' and hub 18 so that the central and peripheral reflectors can rotate relative to eye positioning device 32'.

Figure 12:
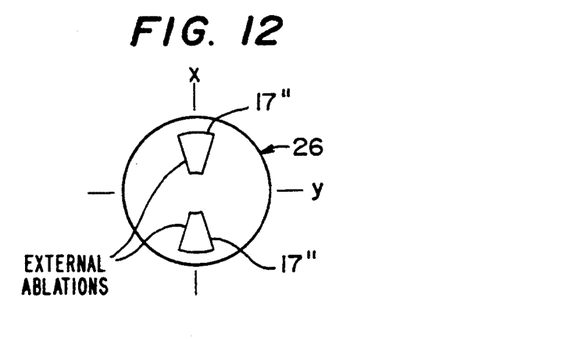
FIG. 12 is a schematic view of a cornea having wedge-shaped ablations on the external surface of the cornea formed by focusing and pivoting radial lines of radiant energy onto external areas of the cornea.

Additionally, a drive assembly 66 having a drive motor 68 for rotating a gear 70 is provided. Gear 70 meshes with a ring gear 72 which is rigidly connected to the sides of the peripheral reflectors. Drive motor 68 is preferably a reversible, stepping motor which allows for incremental rotation of central reflectors 12a–h together with peripheral reflectors 14a–h. Accordingly, the radial lines focused on either the external or internal areas of the cornea can be rotated 360° or pivoted a few degrees in either direction for removing selected portions of the cornea. For example, a pair of radial lines can be focused onto the cornea and pivoted approximately eight degrees from both sides of the X axis to ablate a pair of wedge-shaped incisions 17" as seen in FIG. 12. Of course, cornea 26 can be ablated to remove areas of the cornea having a variety of configurations depending upon various factors such as the number and position of lines, and the amount of rotation.

Figure 7:
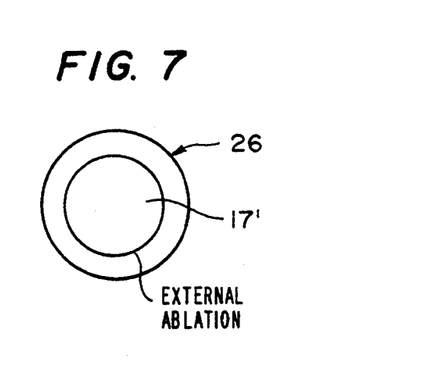
FIG. 7 is a schematic representation of a cornea having a lenticular ablation after scanning the radiant energy beams directed onto the cornea by the apparatus of FIG. 4.

To obtain the scanning pattern schematically shown in FIG. 7 as a full lenticular ablation, drive motor 68 is operated to rotate gear 70 which, in turn, rotates ring 72 to rotate reflectors 12a–h and 14a–h about axis 24. Preferably, the reflectors are rotated at a rate of approximately 200 revolutions per minute. However, rotation speed is preferably selected for the given beam focusing width on the cornea to remove material continuously over the cornea. Conduits 44' can be formed from plates or tubes which are transparent to the radiant energy beam so they do not interfere with the beam. The scanning incision 17' is shown in FIG. 7 and is in the form of a lenticular ablation in the shape of a positive, negative or toxic lens. This ablation includes the full surface of the cornea, although a central part can be omitted, thereby providing an annular ablation. As used herein, "lenticular ablation" means removing corneal material via laser photoablation in the shape of an optical lens.

Figure 5:
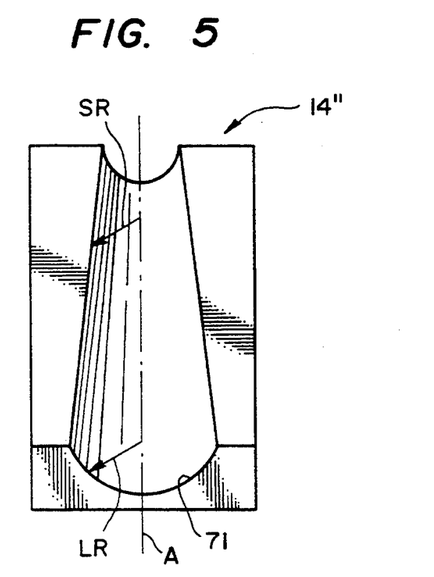
FIG. 5 is a perspective view of a modified peripheral reflector for use in the apparatus of FIG. 1, showing the change in the radius of curvature of the reflector along its central axis A.

Embodiment of FIG. 5

To more precisely tailor the curved line focus of the beams reflected from the peripheral reflectors so that corneas of differing radii of curvature can be accommodated, each peripheral reflector can be designed with a curved reflective surface whose curvature varies along the length of the reflector along central axis A. As shown in FIG. 5, peripheral reflector 14" has a concave surface 71 varying from a smaller radius SR to a larger radius LR. Accordingly, the beams reflected onto the external surface or onto the intrastromal areas of the cornea 26 from reflectors 14" produce radial incisions of desired curved line focus and thus intensity therealong. Reflectors 14" accomplish similar result as reflectors 14a'–h' as seen in FIG. 3 but via a different reflector configuration.

As shown in FIG. 1, the central reflectors can also be provided with four inner and four outer alignment detectors 73 and 74 which monitor the alignment of the reflectors with respect to the beam incident thereon to allow adjustment of the laser beam to the optical center thereof.

The beam delivering apparatus 10 of the present invention controls and focuses the beam on the corneal surface or on intrastromal areas. This is beneficial since the greater the amount of energy radiated onto the cornea, the greater the risk that the cornea will be damaged by overheating or, in the case of ultraviolet radiation, by overshock.

The overall delivery system is quite compact and can be enclosed between the laser 30 and gas conduit system 40' shown in FIG. 4. This allows filling of the whole beam delivering system with a neutral gas to minimize ozone build-up by ultraviolet radiation.

As seen by comparing FIGS. 2 and 4, the arrangement of the central and peripheral reflectors is the same for radial keratotomy and lathing via scanning. The only difference in these procedures is the rotation of the central and peripheral reflectors during scanning.

Figure 9:
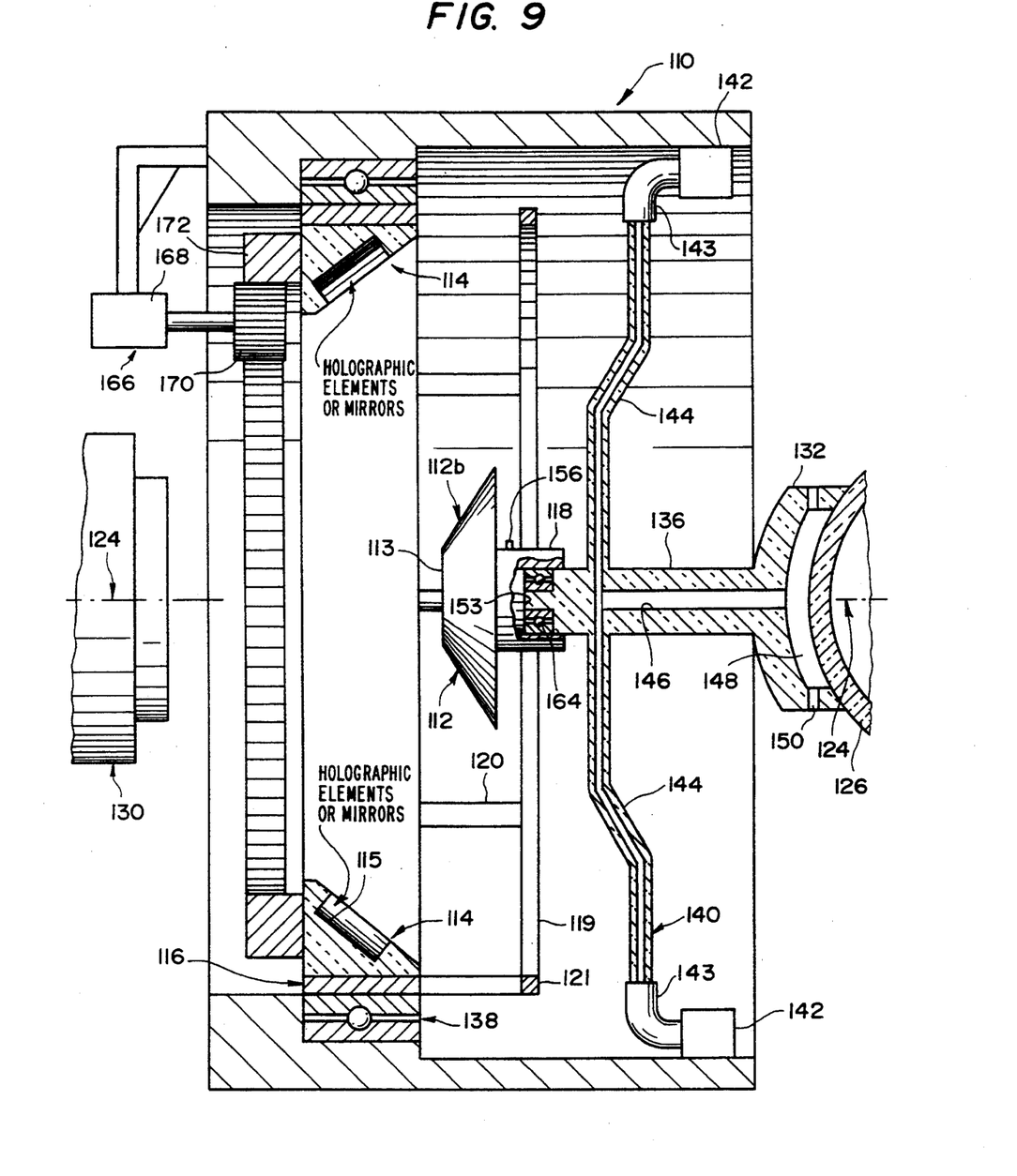
FIG. 9 is a cross-sectional side view of another modification of the apparatus of FIG. 1, having modified peripheral reflectors for ablating circumferentially curved lines either on the external surface of the cornea, or on intrastromal areas of the cornea without disturbing, coagulating or ablating the tissue between the peripheral reflectors and the intrastromal areas to be ablated.

Embodiment of FIG. 9

Referring now to the beam delivering apparatus 110 as shown in FIG. 9, apparatus 110 is substantially identical to the beam delivering apparatus 10 of FIG. 3, except that peripheral reflectors 14a'–h' have been replaced with peripheral reflectors 114a and 114b to simultaneously form two circumferentially curved incisions on areas of a cornea. The circumferentially curved incisions can be formed either on the external surface of a cornea or on intrastromal areas of a cornea.

Specifically, beam delivering apparatus 110 as seen in FIG. 9 includes a pair of central reflectors 112a and 112b and an annular assembly of peripheral reflectors 114a and 114b. Peripheral reflectors 114a and 114b are rigidly coupled to a rim 116. Rim 116 is rigidly coupled to a hub 118 by radial spokes 119, axial rods 120 and a ring 121. Central reflectors 112a and 112b are coupled to hub 118.

Beam delivering apparatus 110 is rotatably supported within a support or frame 122 about a main optical axis 124 which passes through the center of a cornea 126 of an eye. A laser beam source 130, such as a frequency modified YAG laser for ablating external surface areas of the cornea or a frequency-doubled YAG laser for ablating intrastromal areas of the cornea, is positioned to emit a beam along axis 124 and against central reflectors 112a and 112b. These reflectors split and reflect the beam onto peripheral reflectors 114a and 114b which then focus and reflect the split beams onto an area of cornea 126 in a curvilinear configuration.

Referring now more specifically to the construction and orientation of central reflectors 112a and 112b and peripheral reflectors 114a and 114b for performing an operation to correct an astigmatism. A pair of equal sized central reflectors 112a and 112b are provided. While only two central reflectors are illustrated, the number of central reflectors can be any even number more than two and less than 16.

As shown in FIG. 9, two equally sized central reflectors 112a and 112b are rigidly coupled to one another along a pair of opposite sides by a pair of connecting members 113 (only one shown) to form a wedge-shaped mirror centered on axis 124. Each central reflector 112a and 112b is oriented to present a slanted, outwardly facing flat surface to the beam emanating from beam source 130. The angle of each surface is about 50°-60° to axis 124.

Each peripheral reflector 114a and 114b is associated with one of the central reflectors 112a and 112b and is oriented so that its reflective surface 115 intercepts the beam reflected radially, outwardly by its associated central reflector. Additionally, each peripheral reflector is oriented and constructed so as to reflect the intercept beam axially and radially inward and to focus the beam into line focus either onto the external surface of cornea 126 or onto an intrastromal area of the cornea. The line focus of each beam onto cornea 126 is a curvilinear line which is preferably circumferentially curved about the optical axis 124. Preferably, the centers of the circumferentially curved lines focused on cornea 126 are located on optical axis 124.

The reflective surfaces of the central and peripheral reflectors can be curved mirrors or other reflective material which focuses the beam in a curvilinear configuration onto either an external or internal areas of the cornea. For example, the peripheral reflectors 114a and 114b as shown in FIG. 9 are holographic elements or mirrors, which focus circumferential curved lines onto areas of the cornea. Holographic elements or mirrors 114a and 114b can be constructed with a flat reflective surface 115 having different reflective indexes along reflective surface 115 so that a variety of shapes and orientations of lines can be focused onto either external or internal areas of the cornea, including curvilinear lines and rectilinear lines.

Figure 10:
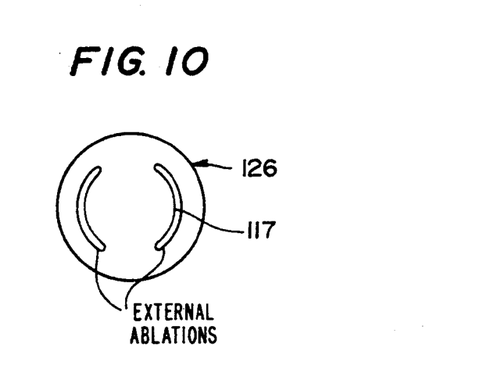
FIG. 10 is a schematic view of a cornea having circumferentially curved incisions on the external surface of the cornea.
Figure 11:
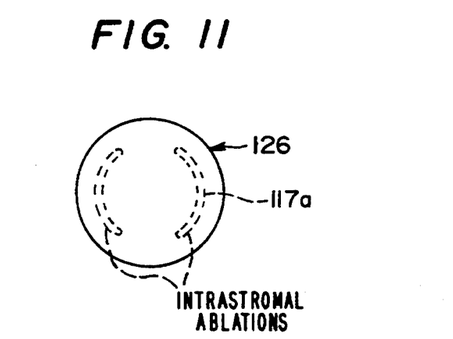
FIG. 11 is a schematic view of a cornea having circumferentially curved incisions on intrastromal areas of the cornea.

As schematically shown in FIG. 10, a two circumferentially curved incisions 117 are cut via photoablation in the external surface of cornea 126 during an operation to correct an astigmatism. Alternatively, two circumferentially curved, intrastromal incisions 117a can be cut via photoablation in intrastromal areas of cornea 126 during an operation to correct an astigmatism, as schematically illustrated in FIG. 11.

Beam delivering apparatus 110 can be used to produce the external or intrastromal incisions simultaneously. As seen in FIG. 9, each central reflector 112a and 112b intercepts the beam and reflects the beam towards its associated peripheral reflector 114a and 114b. Central reflectors 112a and 112b are preferably rotatably coupled to hub 118 via an axle 153 fitting into the hub 118 and a screw adjustment assembly including three set screws 156 to lock the reflectors relative to hub 118. Central reflectors 112a and 112b can be moved as a single unit relative to hub 118 and the adjustment screws 156 can then be operated to adjust and fix the relative position of the central reflectors relative to the peripheral reflectors.

The combination of central and peripheral reflectors including the rim 116, hub 118, spokes 119, rods 120 and ring 121 are supported for rotation relative to frame 122 via ball bearing assembly 138, which is coupled to the frame and to rim 116. Thus, the angular position of the reflectors relative to cornea 126 and axis 124 can be varied. This allows angular placement as desired of either external incisions 117 on the cornea or intrastromal incisions 117a in the cornea.

The operation of beam delivering apparatus 110 during a simple operation to correct an astigmatism is as follows. Cornea 126 is immobilized by appropriate means and laser beam source 130 is positioned to emit a beam along main optical axis 124, which passes through the center of cornea 126. Beam directing apparatus 110 is positioned between beam source 130 and cornea 126 and is appropriately spaced from cornea 126 so that the beams reflected by the central and peripheral reflectors ablate cornea 126 in a pattern comprising separate and discrete areas of ablation shown in FIG. 10 or FIG. 11. Once beam directing apparatus 110 is positioned, a test beam can be emitted to test the alignment of the beams on cornea 126. Beam source 130 is then operated to emit a radiant energy beam, such as a laser beam, which travels along axis 124, encounters the central reflectors 112a and 112b, is split and radially reflected against peripheral reflectors 114a and 114b and is then again radially reflected and focused either onto the external surface of cornea 126 to simultaneously make external incisions 117 or onto intrastromal areas of cornea 126 to simultaneously make intrastromal incisions 117a.

A drive assembly 166 having a drive motor 168 for rotating a gear 170 is provided. Gear 170 meshes with a ring gear 172 which is rigidly connected to the sides of the peripheral reflectors. Drive motor 168 is preferably a reversible, stepping motor which allows for incremental rotation of central reflectors 112a and 112b together with peripheral reflectors 114a and 114b. Accordingly, the circumferentially curved lines, which are focused on either external or internal areas of the cornea, can be rotated 360° or piloted a few degrees to remove selected portions of the cornea.

It should be apparent to those skilled in the art that a plurality of curvilinear lines can be focused onto the cornea at various positions to ablate the cornea as required to correct the patient's vision.

Beam delivering apparatus 110 and eye positioning apparatus 132 can be provided with a gas or fluid conduit system 140 for delivering selected gases to the cornea 126 during ablation. Gas conduit system 140 includes a gas supply means 142 to supply gas along a tube 143 and a conduit 144 mounted within one of the spokes 119. Conduit 144 communicates with an axial conduit 146 within eye positioning apparatus 132 and axial conduit 146 communicates with a substantially semihemispheric recess 148 defined by concave surface 134. Recess 148 communicates with conduit 146 and cornea 126 and has outlets 150 for exhausting gases which have contacted cornea 126.

An inert gas such as argon can be supplied by gas conduit system 140 to contact cornea 126 and remove debris and other by-products of the surgical operation. Additionally, a gas or liquid having a cold temperature, such as, e.g., nitrous oxide, can be supplied by gas conduit system 140 to bathe cornea 126 in a cool environment and thereby lower the metabolic state of the cornea. Lowering the metabolic state of cornea 126 enhances the ability of the cornea to withstand traumatic insults from the beam.

Figure 13:
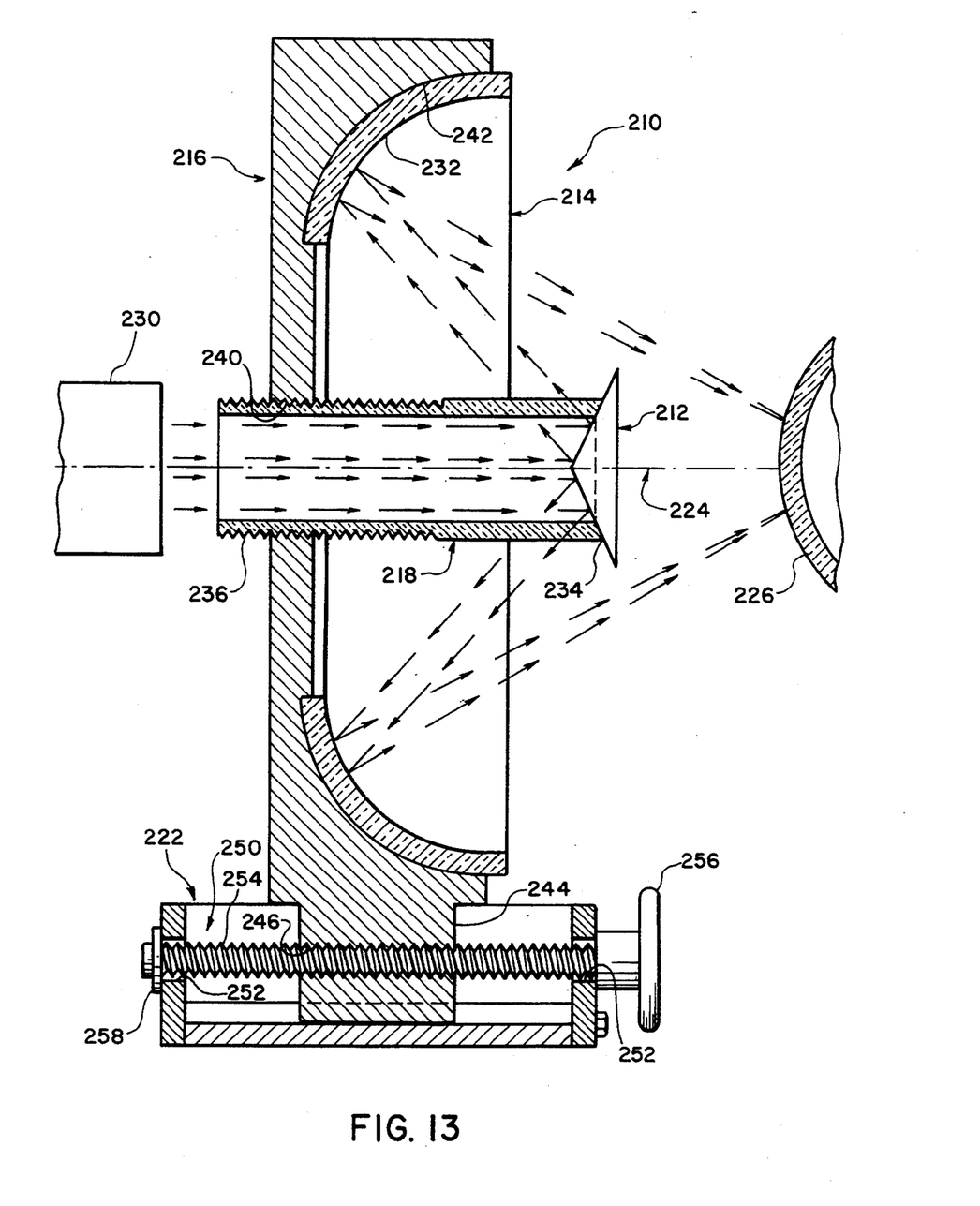
FIG. 13 is a cross-sectional side view of another embodiment of a beam delivering apparatus in accordance with the present invention having a conical or cone-shaped central mirror movably mounted relative to a peripheral mirror by a screw mechanism for ablating circles on the external surface of the cornea, or on intrastromal areas of the cornea without disturbing, coagulating or ablating the corneal tissue located between the peripheral mirror and the intrastromal areas to be ablated.

Embodiment of FIG. 13

Referring now to the beam delivery apparatus 210 illustrated in FIG. 13, the beam delivery apparatus 210 operates in a similar manner as the beam delivery apparatus 10 of FIGS. 1–2, except that beam delivery apparatus 210 is designed for creating circular or non-circular ablations either on the exterior surface of the cornea or intrastromal area of the cornea 226.

Apparatus 210 basically includes a central reflector or mirror 212 and an annular peripheral mirror 214. Peripheral mirror or reflector 214 is rigidly coupled to a rim 216 for movement therewith, while central mirror or reflector 212 is movably coupled to rim 216 via a transparent hub 218. Relative movement between central reflector 212 and peripheral reflector 214 can be used to change the position of focus of the ring-shaped beam of energy on the cornea 226. Accordingly, this relative movement between central reflector 212 and peripheral reflector 214 can be used to scan the ring-shaped beam of energy across cornea 226 for reprofiling the cornea 226. This allows very complicated shapes to be produced, including bifocal and multi-focal shapes.

Beam delivery apparatus 210 is movably supported on a support frame or screw mechanism 222 for axial movement along a main optical axis 224 which passes through the center of a cornea 226 of an eye. A laser beam source 230, such as a frequency modified 5th Harmonic YAG laser for ablating external surface areas of the cornea or a frequency-doubled YAG laser for ablating intrastromal areas of the cornea, is positioned to emit a beam along optical axis 224 and against central mirror or reflector 212. The central reflector 212 splits and reflects the laser beam onto the peripheral reflector 214 which then focuses and reflects the laser beam onto the cornea 226 in the form of a circle or non-circular ring-shaped line.

Central reflector 212 is preferably a conical or cone-shaped mirror positioned with its longitudinal axis on the main optical axis 224 for receiving the laser beam from laser beam source 230. The slope of central reflector 212 is such that the laser beam is reflected outwardly against peripheral reflector 214. Central reflector 214 is movably coupled relative to peripheral reflector 214 by hub 218. Of course, central reflector 212 and peripheral reflector 214 can also be holographic elements which are capable of producing non-circular ring-shaped beams of energy. Moreover, reflectors 212 and 214 can be constructed to produce either continuous ring-shaped beams or discontinuous ring-shaped beams.

Hub 218 is a cylindrical transparent tube with a first end 234 rigidly and fixedly coupled to central reflector 212 and a second threaded end 236 for threadedly engaging rim 216. Hub 218 is concentrically mounted about the laser beam for receiving the laser beam through the center of the tubular hub 218.

Rim 216 has a centrally located threaded opening 240 for threadedly receiving second end 236 of hub 218 therein, and an annular curved recess 242 for fixedly mounting peripheral reflector 214 therein. Rim 216 also includes a downwardly extending T-shaped block 244 with a threaded bore 246 for movably mounting rim 216 as well as central reflector 212 and peripheral reflector 214 parallel to the main optical axis 224. In other words, rim 216 is movably mounted to move both the central reflector 212 and the peripheral reflector 214 closer to or farther away from laser beam source 230. Thus, by moving both reflectors 212 and 214 together, it is possible to scan the ring-shaped beam of energy across cornea 226 for reprofiling cornea 226.

Support frame 222 has a T-shaped slot 250 for slidably receiving T-shaped block 244 of rim 216 therein. Support frame 222 also has a pair of axially extending bore 252 for receiving a threaded shaft 254. Threaded shaft 254 has a handle 256 fixedly coupled to one end and a C-clip 258 fixedly coupled to the other end for rotatably securing shaft 254 within bore 252. When T-shaped block 244 is received within T-shaped slot 250 of support frame 222, threaded bore 246 aligns with bore 252 for threadedly receiving shaft 254 therein. Accordingly, as threaded shaft 254 is rotated via handle 256, T-shaped block 244 is moved longitudinally within T-shaped slot 250.

Peripheral reflector 214 is oriented so that its reflective surface 232, which is curved about a horizontal axis and a vertical axis, forms a ring-shaped spherical surface. Accordingly, peripheral reflector 214 is oriented to intercept the laser beam reflected radially outwardly by the central reflector 212. Additionally, peripheral reflector 214 is oriented to reflect the intercepted beam axially and radially inwardly and to focus the beam of energy into a ring-shaped line focus or configuration either onto the external surface of cornea 226 or onto an intrastromal area of the cornea 226. The reflective surfaces of the central and peripheral reflectors 212 and 214 can be mirrors or other reflective material. For example, the central and peripheral reflectors can be constructed of holographic elements capable of producing a linearly focused beam of energy with a complex or irregular shape.

Figure 15:
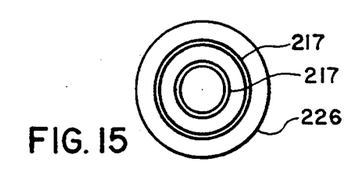
FIG. 15 is a schematic view of a cornea having a pair of circular incisions on the external surface of the cornea.
Figure 16:
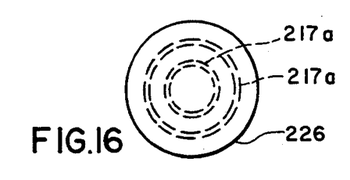
FIG. 16 is a schematic view of a cornea having a pair of circular incisions on intrastromal areas of the cornea.

The operation of beam delivery apparatus 210 during a corneal modification operation is as follows: cornea 226 is immobilized by appropriate means and laser beam source 230 is positioned to emit a beam along main optical axis 224, which passes through the center of cornea 226. Beam directing apparatus 210 is positioned between beam source 230 and cornea 226 at an appropriate distance from cornea 226 so that the beams reflected by the central and peripheral reflectors 212 and 214 ablate cornea 226 in a circular or ring-shaped line configuration as shown in FIGS. 15 or 16. Of course, depending on the shape or construction of reflectors 212 and 214, irregular or non-circular ring-shaped patterns may be focused onto cornea 226 for reprofiling cornea 226 to the desired shape.

Once beam delivering apparatus 210 is positioned, a test beam can be admitted to test the alignment of the beams on cornea 226. Beam source 230 is then operated to emit a radiant energy beam, such as a laser beam, which travels along optical axis 224 to strike central reflector 212. Central reflector 212 then splits and radially reflects the energy beam against peripheral reflector 214. Peripheral reflector 214 then reflects and focuses the ring-shaped beam of energy either onto the external surface of the cornea to create an incision such as a circular incision 217 illustrated in FIG. 15 or onto intrastromal areas of the cornea 226 to make an incision such as intrastromal incision 217a illustrated in FIG. 16.

Moreover, the ring-shaped beam of energy may be focused by peripheral reflector 214 in front of the external surface cornea 226, or behind the external surface of the cornea 226, to ablate a wider ring-shaped portion of the cornea 226, than when the ring-shaped beam is focused on the external surface of cornea 226.

When desired, the focused, ring-shaped beam of energy may be scanned or moved across the cornea to reprofile or reshape the cornea. In particular, both the central and peripheral reflectors 212 and 214 are moved together either closer to or farther from cornea 226 by the screw mechanism 222 to scan the ring-shaped beam of energy across cornea 226. Thus, the line focus of light is scanned across cornea 226 for ablating portions of the cornea to reprofile the cornea into the desired shape.

The scanning of the line focus of energy or the ring-shaped beam of energy across cornea 226 can also be accomplished either by using the central reflector 212 relative to the peripheral reflector 214 or by moving the beam focusing device 320 as discussed below. In any event, the energy applied onto the portion of the cornea to be ablated or otherwise modified can be controlled by the scanning speed of the beam across the cornea and/or by changing the point of focus. Accordingly, very complex and precise reshaping of the cornea is possible using the beam delivery apparatus 210 by controlled scanning of the cornea with a circular or non-circular ring-shaped beam of energy. Specifically, the cornea can be reprofiled to change the contour of the cornea by controlling or varying the amount of time and/or energy in which the beam of energy is delivered onto the cornea for ablating or otherwise modifying the cornea.

Figure 14:
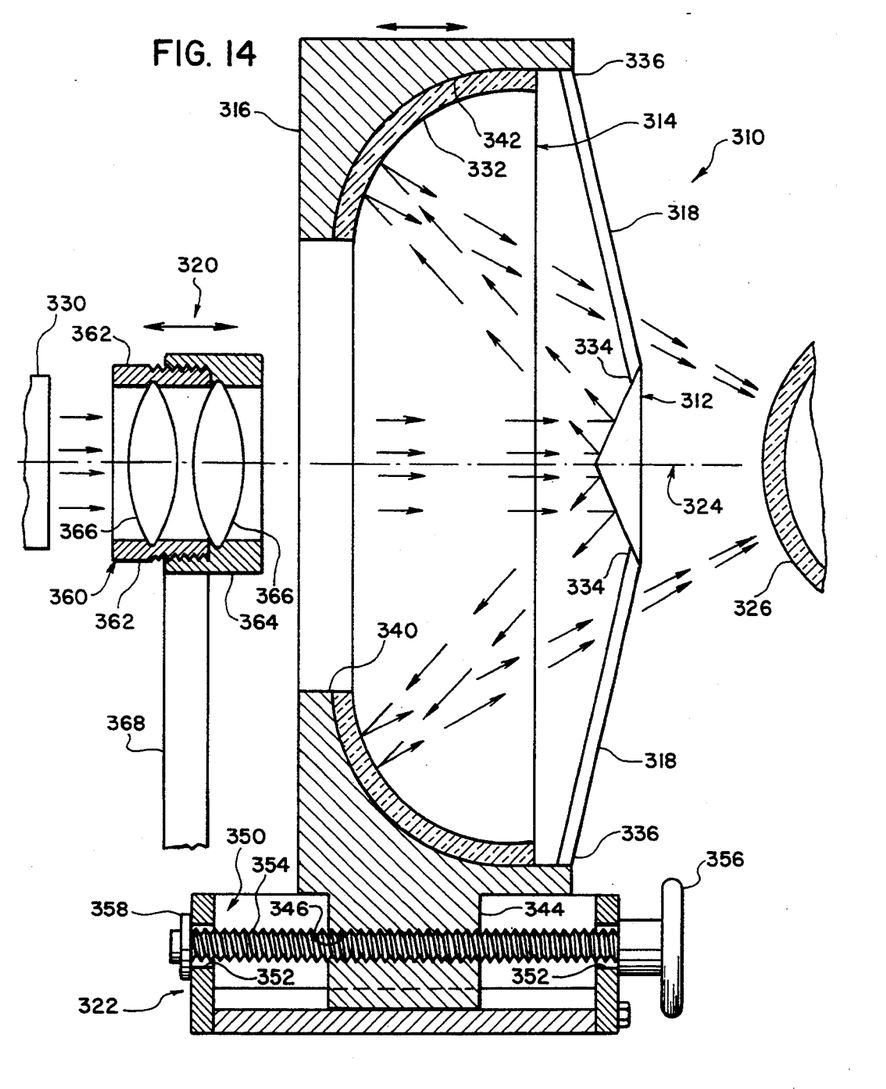
FIG. 14 is a cross-sectional side view of another modification of the beam delivering apparatus of FIG. 13, having a plurality of lenses movably positioned between the laser beam and the central mirror, which is fixedly mounted to the peripheral mirror so that movement of the lenses change the angle of the laser beam hitting the central mirror.

Embodiment of FIG. 14

Referring now to the beam delivering apparatus 310 illustrated in FIG. 14, the beam delivering apparatus 310 basically includes a central mirror or reflector 312, a peripheral mirror or reflector 314 rigidly coupled to central reflector 312 via a rim 316 and a plurality of transparent spokes 318, and a laser beam focusing device 320. Beam delivering device 310 is substantially identical to beam delivering device 210, except that beam delivering device 310 has its central reflector 312 fixedly coupled to rim 316 and a beam focusing device 320 has been added.

Peripheral reflector 314 is rigidly coupled to rim 316 for movement therewith, while central reflector 12 is fixedly coupled to rim 316 via transparent spokes 318.

Beam delivery apparatus 310 is movably supported on a support frame or screw mechanism 322 for axial movement along a main optical axis 324 which passes through the center of a cornea 326 of an eye. A laser beam source 330, such as a frequency modified 5th Harmonic YAG laser for ablating external surface areas of the cornea or a frequency-doubled YAG laser for ablating intrastromal areas of the cornea, is positioned to emit a beam of radiant energy along optical axis 324 and against central reflector 312. The central reflector 312 splits and reflects the laser beam onto the peripheral reflector 314 which then focuses and reflects the laser beam onto the cornea 326 in the form of a circle or non-circular ring-shaped line.

Central reflector 312 is preferably a conical or cone-shaped mirror positioned with its longitudinal axis on the main optical axis 324 for receiving the laser beam from laser beam source 330. The slope of central reflector 312 is such that the laser beam is reflected outwardly against peripheral reflector 314. Central reflector 314 is fixedly coupled to peripheral reflector 314 by spokes 318.

Spokes 318 are transparent members. Each spoke 318 has a first end 334 rigidly and fixedly coupled to central reflector 312 and a second threaded end 336 rigidly and fixedly to rim 316.

Rim 316 has a centrally located opening 340 for receiving the laser beam therethrough, and an annular curved recess 342 for fixedly mounting peripheral reflector 314 therein. Rim 316 also includes a downwardly extending T-shaped block 344 with a threaded bore 346 for movably mounting rim 316 as well as central reflector 312 and peripheral reflector 314 parallel to the main optical axis 324. In other words, rim 316 is movably mounted to move both the central reflector 312 and the peripheral reflector 314 closer to or farther away from laser beam source 330. Thus, by moving both reflectors 312 and 314 together, it is possible to scan the ring-shaped beam of energy across cornea 326 for reprofiling cornea 326.

Support frame 322 has a T-shaped slot 350 for slidably receiving T-shaped block 344 of rim 316 therein. Support frame 322 also has an axially extending bore 352 for receiving a threaded shaft 354. Threaded shaft 354 has a handle 356 fixedly coupled to one end and a C-clip 358 fixedly coupled to the other end for rotatably securing shaft 354 within bore 352. When T-shaped block 344 is received within T-shaped slot 350 of support frame 322, threaded bore 346 aligns with bore 352 for threadedly receiving shaft 354 therein. Accordingly, as threaded shaft 354 is rotated via handle 356, T-shaped block 344 is moved longitudinally within T-shaped slot 350.

Peripheral reflector 314 is oriented so that its reflective surface 332, which is curved about a horizontal axis and a vertical axis so as to form a spherical surface. Accordingly, peripheral reflector 314 is oriented to intercept the laser beam reflected radially outwardly by the central reflector 312. Additionally, peripheral reflector 314 is oriented to reflect the intercepted beam axially and radially inwardly and to focus the beam of energy into a circular or non-circular ring-shaped line configuration either on the external surface of cornea 326 or onto an intrastromal area of the cornea 326. The reflective surfaces of the central and peripheral reflectors 312 and 314 can be mirrors or other reflective material. For example, the central and peripheral reflectors can be constructed of holographic elements capable of producing a linear focused beam of energy with a complex or irregular shape.

Beam focusing device 320 includes an adjustable cylindrical support member 360 with a first half 362 movably coupled to a second half 364, a pair of lenses 366 with one fixedly coupled within each one of the halves of the support member 360, and a movable support frame 368 coupled to support member 360 for moving lenses 366 together along the main optical axis 324. Accordingly, lenses 366 can be moved relative to each other along main optical axis 324 for changing the focus of the output beam onto the central reflector 312, and thus, change the focus of the output beam on the cornea. For example, first and second halves 362 and 364 of support member 360 are threadedly coupled together such that threading or unthreading the halves 362 and 364 relative to one another causes the lenses 366 to move relative to each other along main optical axis 324. Of course, other types of adjusting mechanism can be utilized to move the two lenses 366 relative to each other.

Beam focusing device 320 is moved axially along main optical axis 324 for changing the focus of the beam from laser beam source 330 onto an area of the cornea. Accordingly, by axially moving beam focusing device 320 along the main optical axis 324, larger or smaller circular portions of cornea 326. Thus, beam focusing device 320 regulates the size or diameter of the ring-shaped portion to be ablated from the cornea 326 by changing the incident of light from the laser beam source on central reflector 312. In other words, by moving beam focusing device 320 along the main optical axis 324, the location of the ring-shaped beam on the cornea can be adjusted.

Beam focusing device 320 can also be used for scanning the ring-shaped beam across the cornea to reprofile the cornea. In particular, by moving beam focusing device 320 along the main optical axis 324, the linear focus of the ring-shaped beam can be scanned across the cornea to achieve complex reshaping of the cornea. Depending on the rate of movement of beam focusing device 320, the ring-shaped beam can be scanned at either a constant rate or a variable rate to produce a smooth cornea surface and to achieve aspheric or multi-focal shapes. Of course, beam focusing device 320 can be used with the other beam delivering apparatuses discussed above if needed or desired.

The operation of beam delivery apparatus 310 during a corneal modification operation is as follows: cornea 326 is immobilized by appropriate means and laser beam source 330 is positioned to emit a beam along main optical axis 324, which passes through the center of cornea 326. Beam directing apparatus 310 is positioned between beam source 330 and cornea 326 at an appropriate distance from cornea 226 so that the beams reflected by the central and peripheral reflectors 312 and 314 ablate cornea 326 in a circular ring-shaped line configuration as shown in FIGS. 15 or 16. Of course, depending on the shape and/or construction of reflectors 312 and 314, irregular or non-circular ring-shaped line configurations may be focused onto cornea 326 for reprofiling cornea 326 to the desired shape.

Once beam delivering apparatus 310 is positioned, a test beam can be admitted to test the alignment of the beams on cornea 326. Beam focusing device 320 can be moved along main optical axis 324 to regulate the diameter of ring-shaped portion to be ablated from the cornea 326. Beam source 330 is then operated to emit a radiant energy beam, such as a laser beam, which travels along optical axis 324 to strike central reflector 312. Central reflector 312 then splits and radially reflects the energy beam against peripheral reflector 324. Peripheral reflector 314 then reflects and focuses the ring-shaped beam of energy either onto the external surface of the cornea to create an incision such as a circular or ring-shaped incision 217 illustrated in FIG. 15, or onto intrastromal areas of the cornea 326 to make an intrastromal incision such as incision 217a illustrated in FIG. 16.

Moreover, the ring-shaped beam may be focused by the peripheral reflector 314 either behind or in front of the external surface of cornea 326 to provide a wider ring-shaped incision than if the ring-shaped beam is focused on the external surface of the cornea 326.

When desired, the focused, ring-shaped beam of energy may be scanned or moved across the cornea to reprofile or reshape the cornea. In particular, both the central and peripheral reflectors 312 and 314 are moved together either closer to or farther from cornea 326 by the screw mechanism 322 to scan the ring-shaped beam of energy across cornea 326. Thus, the line focus of light is scanned across cornea 326 for ablating portions of the cornea to reprofile the cornea into the desired shape.

The scanning of the line focus of energy or the ring-shaped beam of energy across cornea 326 can also be accomplished either by using the central reflector 312 relative to the peripheral reflector 314 or by moving the beam focusing device 320. When using beam focusing device 320, scanning of the ring-shaped beam of energy can be accomplished by moving the entire beam focusing device 320 along the main optical axis 324 or by moving the lenses 366 relative to each other.

In any event, the energy applied onto the portion of the cornea to be ablated or otherwise modified can be controlled by the scanning speed of the beam across the cornea and/or by changing the point of focus. Accordingly, very complex and precise reshaping of the cornea is possible using the beam delivery apparatus 310 by controlled scanning of the cornea with a circular or non-circular ring-shaped beam of energy. Specifically, the cornea can be reprofiled to change the contour of the cornea by controlling or varying the amount of time and/or energy in which the beam of energy is delivered onto the cornea for ablating or otherwise modifying the cornea.

While various advantageous embodiments have been chosen to illustrate the invention, it will be understood by those skilled in the art that various changes and modifications can be made therein without departing from the scope of the invention as defined in the appended claims.

What is claimed is:

1. An apparatus for delivering radiant energy beams onto an optical area of an eye centered on an optical axis extending from the eye, comprising:

a source of radiant energy beam aimed along the optical axis for emitting a radiant energy beam having a wavelength capable of ablating a predetermined area of an eye;

a support;

a central reflector arranged in stable optical communication with the source of radiant energy beam and positioned along the optical axis for intercepting the radiant energy beam incident thereon, splitting the beam into a continuous, ring-shaped beam, and reflecting the ring-shaped beam outwardly of the optical axis;

first coupling means, coupled to said support and said central reflector, for coupling said central reflector to said support;

a peripheral reflector spaced outwardly from said central reflector for intercepting said ring-shaped beam reflected from said central reflector for directing said ring-shaped beam along the optical axis and for incidence onto the optical area of the eye, said peripheral reflector including means for focusing said ring-shaped beam onto an area of the eye in a ring-shaped line configuration; and second coupling means, coupled to said support and said peripheral reflector, for coupling said peripheral reflector to said support.

2. An apparatus according to claim 1, wherein said means for focusing is configured to focus said intercepted beam portion onto an intrastromal area of a cornea without ablating an external surface of the cornea.

3. An apparatus according to claim 1, wherein said means for focusing is configured to focus said intercepted beam portion onto an external area of a cornea for ablating an external surface of the cornea.

4. An apparatus according to claim 1, further comprising
adjusting means, positioned between said source of said radiant energy beam and said central reflector, for regulating size of said ring-shaped line configuration on the optical area and for scanning said ring-shaped line configuration across the optical area.

5. An apparatus according to claim 4, wherein said adjusting means includes at least two lenses.

6. An apparatus according to claim 1, wherein said first coupling means movably couples said central reflector to said support for changing relative position between said central reflector and said peripheral reflector to change size of said ring-shaped line configuration on a cornea.

7. An apparatus according to claim 6, wherein said first coupling means includes a transparent tubular member movably coupling said central reflector to said support with said tubular member positioned along the optical axis.

8. An apparatus according to claim 7, wherein said central reflector has a cone-shaped reflective surface.

9. An apparatus according to claim 8, wherein said means for focusing comprises a partially spherical reflective surface.

10. An apparatus according to claim 8, wherein said means for focusing comprises a reflective surface that is curved about an axis A and is curved about an axis B which is perpendicular to axis A.

11. An apparatus according to claim 8, and further comprising
said peripheral reflector includes at least one holographic element.

12. A method of modify an area of an optical surface via a radiant energy beam, comprising the steps of
aligning a source of radiant energy beam and the optical surface to be modified along an optical axis extending from the eye,
emitting the radiant energy beam from the source along the optical axis,
splitting the beam into a ring-shaped beam and reflecting the ring-shaped beam outwardly of the optical axis by using a first reflector,
reflecting the outwardly directed ring-shaped beam along the optical axis by using a second reflector to produce a ring-shaped output beam, and
directing and focusing the ring-shaped output beam via the second reflector for incidence on the optical surface to be modified in a ring-shaped line configuration.

13. A method according to claim 12, wherein the directing and focusing step includes focusing the ring-shaped line configuration of the output beam onto intrastromal areas of a cornea for ablating the intrastromal areas without ablating an external surface of the cornea.

14. A method according to claim 12, wherein the directing and focusing step includes focusing the ring-shaped line configuration of the output beam portion onto external areas of a cornea for ablating the external areas of the cornea.

15. A method according to claim 12, wherein the directing and focusing step includes focusing the ring-shaped line configuration of the output beam in front of an external surface of a cornea for ablating a wide ring-shaped portion of the external surface of the cornea.

16. A method according to claim 12, wherein the directing and focusing step includes focusing the ring-shaped line configuration of the output beam behind an external surface of a cornea for ablating a wide ring-shaped portion of the external surface of the cornea.

17. A method according to claim 12, further comprising the step of
adjusting size of said ring-shaped line configuration of the output beam.

18. A method according to claim 12, wherein the splitting step, the reflecting step, and the directing and focusing step include the step of scanning the ring-shaped line configuration of the output beam across a portion of the optical surface to be modified.

19. A method according to claim 18, wherein the scanning step includes moving the ring-shaped line configuration along a radial path extending from the optical axis.

20. A method according to claim 19, wherein the scanning step includes using a beam focusing device positioned along the optical axis prior to the splitting step to scan the ring-shaped line configuration of the output beam across a portion of the optical surface to be modified.

21. A method according to claim 19, wherein the scanning step includes moving a central reflector used for splitting the radiant energy beam from the source in the splitting step relative to a peripheral reflector used for producing the output beam in the reflecting step.

22. A method according to claim 19, wherein the directing and focusing step includes focusing the ring-shaped line configuration output beam portion onto intrastromal areas of a cornea for ablating the intrastromal areas without ablating an external surface of the cornea.

23. A method according to claim 19, wherein the directing and focusing step includes focusing the ring-shaped line configuration of the output beam onto external areas of the cornea for ablating the external areas of the cornea.

24. A method according to claim 19, wherein the directing and focusing step includes focusing the ring-shaped line configuration of the output beam in front of an external surface of a cornea for ablating a wide ring-shaped portion of the external surface of the cornea.

25. A method according to claim 19, wherein the directing and focusing step includes focusing the ring-shaped line configuration of the output beam behind an external surface of a cornea for ablating a wide ring-shaped portion of the external surface of the cornea.

26. A method of modifying an optical surface of an eye with an external surface via a radiant energy beam, comprising the steps of
    aligning a source of radiant energy beam and the eye along an optical axis extending from the eye,
    emitting the radiant energy beam from the source along the optical axis,
    splitting the beam into at least one beam portion and reflecting the at least one beam portion outwardly of the optical axis by using a first reflector,
    reflecting the outwardly directed beam portion along the optical axis by using a second reflector to produce at least one output beam portion,
    reflectively directing and focusing the at least one output beam portion via the second reflector for incidence on the optical surface in a linear focused configuration, and
    scanning the linear focused configuration of the at least one output beam across the optical surface.

27. A method according to claim 26, wherein
    the directing and focusing step includes focusing a ring-shaped line configuration of the output beam onto intrastromal areas of a cornea of the eye for ablating the intrastromal areas without ablating an external surface of the cornea.

28. A method according to claim 26, wherein
    the directing and focusing step incudes focusing a ring-shaped line configuration of the output beam portion onto external areas of the cornea for ablating the external areas of the cornea.

29. A method according to claim 26, wherein
    the directing and focusing step includes focusing a ring-shaped line configuration of the output beam in front of an external surface of a cornea for ablating a wide ring-shaped portion of the external surface of the cornea.

30. A method according to claim 26, wherein
    the directing and focusing step includes focusing a ring-shaped line configuration of the output beam behind an external surface of a cornea for ablating a wide ring-shaped portion of the external surface of the cornea.

31. A method of modifying an optical surface of an eye with an external surface via a radiant energy beam, comprising the steps of
    aligning a source of radiant energy beam and the eye along an optical axis extending from the eye,
    emitting the radiant energy beam from the source along the optical axis,
    splitting the beam into at least one beam portion and reflecting the at least one beam portion outwardly of the optical axis by using a first reflector,
    reflecting the outwardly directed beam portion generally along the optical axis to produce at least one output beam portion by using a second reflector, and
    reflectively directing and focusing the at least one output beam portion via the second reflector for incidence on the optical surface in a linear focused configuration for modifying the optical surface.

32. A method according to claim 31, wherein
    the directing and focusing step includes focusing the output beam portions in a rectilinear configuration on the optical surface to be modified.

33. A method according to claim 31, wherein
    the splitting, the two reflecting, and the directing and focusing steps include the step of revolving the output beam portions about the optical axis of the eye.

34. A method according to claim 31, wherein
    the directing and focusing step includes focusing the output beam portions in a curvilinear configuration on the optical surface to be modified.

* * * * *

UNITED STATES PATENT AND TRADEMARK OFFICE
CERTIFICATE OF CORRECTION

PATENT NO. : 5,425,727
DATED : June 20, 1995
INVENTOR(S) : Jeffrey E. Koziol

It is certified that error appears in the above-indentified patent and that said Letters Patent is hereby corrected as shown below:

On the title page: Item [63] Related U.S. Application Data, line 2, "abandoned" should be replaced with -- Pat. No. 5,364,388 --.
Column 1, line 7, "abandoned" should be replaced with -- U.S. Pat. No. 5,364,388 --.

Signed and Sealed this

Twenty-eighth Day of May, 1996

Attest:

BRUCE LEHMAN

*Attesting Officer*  *Commissioner of Patents and Trademarks*